(12) United States Patent
Schmiesing et al.

(10) Patent No.: US 6,544,179 B1
(45) Date of Patent: Apr. 8, 2003

(54) ULTRASOUND IMAGING SYSTEM AND METHOD HAVING AUTOMATICALLY SELECTED TRANSMIT FOCAL POSITIONS

(75) Inventors: Daniel C. Schmiesing, Granite Falls, WA (US); Cedric Chenal, Kirkland, WA (US); Lars Jonas Olsson, Woodinville, WA (US)

(73) Assignee: Koninklijke Philips Electronics, NV (NL)

( * ) Notice: Subject to any disclaimer, the term of this patent is extended or adjusted under 35 U.S.C. 154(b) by 0 days.

(21) Appl. No.: 10/023,080

(22) Filed: Dec. 14, 2001

(51) Int. Cl.$^7$ .................................................. A61B 8/00
(52) U.S. Cl. ........................................................ 600/447
(58) Field of Search .............................. 600/443, 437, 600/447, 458; 73/625–626

(56) References Cited

U.S. PATENT DOCUMENTS

| | | | |
|---|---|---|---|
| 4,566,459 A | * 1/1986 | Umemura et al. ............. 73/597 |
| 4,979,500 A | * 12/1990 | Hassler et al. ............... 600/439 |
| 5,072,735 A | 12/1991 | Okazaki et al. ......... 128/660.07 |
| 5,301,552 A | * 4/1994 | Nagura et al. ................. 73/606 |
| 5,357,962 A | 10/1994 | Green .................... 128/660.07 |
| 5,553,499 A | 9/1996 | Hisata et al. .................. 73/606 |
| 5,581,517 A | 12/1996 | Gee et al. ..................... 367/138 |
| 5,720,289 A | 2/1998 | Wright et al. .......... 128/660.07 |
| 5,740,805 A | 4/1998 | Dolazza et al. ......... 128/660.06 |
| 5,974,891 A | 11/1999 | Uchikawa et al. ............. 73/625 |
| 6,106,465 A | 8/2000 | Napolitano et al. ......... 600/443 |
| 6,146,330 A | * 11/2000 | Tujino et al. ................ 600/443 |
| 6,168,564 B1 | 1/2001 | Teo .............................. 600/443 |
| 6,172,939 B1 | 1/2001 | Cole et al. ..................... 367/138 |
| 6,217,516 B1 | 4/2001 | Poland et al. ................ 600/437 |
| 6,315,723 B1 | 11/2001 | Robinson et al. ........... 600/443 |

* cited by examiner

*Primary Examiner*—Francis J. Jaworski
(74) *Attorney, Agent, or Firm*—Dorsey & Whitney, LLP

(57) ABSTRACT

An ultrasound imaging system includes an ultrasound scanhead coupled to an image processor that causes ultrasound images to be generated on the viewing screen of a display. The image processor includes a beamformer generating transmit and receive beams, a signal processor and a conventional scan converter. The signal processor receives signals from the beamformer to generate image data corresponding to an image, analyzes the image data and, based on the analysis, determines the number of transmit focal positions that should be used as well as the optimum location for each focal position. The signal processor then couples data to the beamformer to set the location of the focal position(s).

30 Claims, 11 Drawing Sheets

ULTRASOUND IMAGING SYSTEM AND METHOD HAVING AUTOMATICALLY SELECTED TRANSMIT FOCAL POSITIONS

TECHNICAL FIELD

This invention relates to diagnostic ultrasound imaging, and, more particularly, to a system and method for automatically selecting the position of one or more focal positions of a transmitted ultrasound beam.

BACKGROUND OF THE INVENTION

Ultrasound can be used to image tissues and vessels using a variety of imaging modalities. For example, B-mode scanning can be used to image tissues by portraying the tissues in a gray scale in which the brightness of each region of the image is a function of the intensity of ultrasound returns from corresponding regions of the tissues. B-mode scanning can be used to visualize the shapes of organs and vessels, and to detect the presence of masses, such as tumors, in tissues. Doppler scanning can be used to provide images showing the velocity of moving sound reflectors, such as blood flowing through an artery or vein. Using Doppler scanning to image the flow pattern of blood through a vessel allows the internal shape of the vessel to be inferred. As a result, partial obstructions in blood vessels can be detected.

A conventional diagnostic ultrasound imaging system 10 is shown in FIG. 1. The ultrasound imaging system 10 includes a scanhead 20 having a transducer face that is placed in contact with a target area containing tissues, organs or blood vessels of interest. As explained below, the scanhead 20 includes an array of transducer elements 24 each of which transforms a transmit signal into a component of an ultrasound beam and transforms an ultrasound reflection into a respective receive signal. These signals are coupled between the scanhead 20 and an imaging unit 30 through a cable 26. The imaging unit 30 is shown mounted on a cart 34. The imaging system also includes a control panel 38 for allowing a user to interface with the system 10. A display monitor 40 having a viewing screen 44 is placed on an upper surface of the imaging unit 30.

In operation, the transducer elements 24 in the scanhead 20 collectively transmit a beam 50 of ultrasound energy as shown in FIG. 2. Respective electrical signals, typically at a frequency of 1–20 MHz, are applied to all or some of the transducer elements 24. The number of transducer elements 24 to which electrical signals are applied determines the size of the transmit aperture. The size of the aperture affects the size of the imaging field and resolution, as explained below. In practice, the phases of the electrical signals applied to the transducer elements 24 are adjusted so that the beam 50 is focused in a focal position 52. The depth to the focal position 52 beneath the transducer face is controlled by the magnitude of the differences in phase of the electrical signals applied to the transducer elements 24. The focal length, which corresponds to the effective length of the focal position 52, is determined by the size and gain of the transmit aperture, i.e., the number of transducer elements 24 used to form the beam 50. The focal position 52 should ideally be positioned where features of maximum interest are located so that these features will be in the best attainable focus. The focal position 52 is shown for illustrative purposes in FIG. 2 as being considerably "sharper" than typical in practice. The ultrasound from the individual transducer elements 24 is normally diffracted by tissues so that the effective length of the focal position 52 is actually more of an area where the beam 50 is narrowed rather than a location where the beam 50 comes to a point.

As previously mentioned, the transducer elements 24 are also used to receive ultrasound reflections and generate corresponding electrical signals. As shown in FIG. 3, the phase and gain of the received signals are also adjusted to effectively generate a receive beam 56 that is focused to a focal position 58 corresponding to the phase differences between the signals coupled from the transducer elements 24. (In the interest of clarity, beam components for only two transducer elements 24 are shown, although it will be understood that beam components would exist for all active transducer elements). The receive beam 56 can also be "steered," i.e., offset from an axis that is perpendicular to the transducer face, by adjusting the phase differences between the signals coupled from the transducer elements 24. In practice, the phase differences between these signals are adjusted as a function of time delay from each ultrasound transmission so that the focal position 58 dynamically varies with depth from a relatively deep position 60 to a relatively shallow position 62 from where the ultrasound is reflected. Thus, in contrast to the constant position of focal position 52 for the transmit beam 50, the focal position 58 for the receive beam 56 varies dynamically with the depth from where the ultrasound is reflected. As explained below, the disclosed invention relates to the locations of the focal position 52 for the transmit beam 50 rather than the locations of the focal position 58 for the receive beam 56.

A typical B-mode ultrasound image 64 is displayed on the viewing screen 44 as shown in FIG. 4. The ultrasound image 64 shows a number of anatomical features, such as tissues 66 and a blood vessel 68. In the specific case shown in FIG. 4, the area of interest to the medical practitioner is the vessel 68. As a result, the focal position of the transmit beam should ideally be located at the depth of the vessel 68. The conventional ultrasound imaging system 10 (FIG. 1) has the ability to adjust the location of the transmit beam focal position. As shown in FIG. 4, the location of the focal position along the depth axis of the image 64 is indicated by a cursor 70 on the right hand side of the viewing screen 44. The location of the focal position is adjusted by suitable means, such as by manipulating a control on the control panel 38 (FIG. 1). As a result, a medical practitioner can place the focal position of the transmit beam at the area of greatest interest in the ultrasound image 64.

It is possible for objects of interest to be larger than can be effectively focused by a single focus position, or that there are multiple objects at different depths of field, which cannot be adequately focused by a single focus position. One solution to this problem is provided by the conventional ultrasound imaging system 10 generating an image using two or more transmit focal positions, as shown in FIG. 5. The viewing screen 44 shows a B-mode image 80 showing tissues 82 containing a relatively large blood vessel 84. A single focal region may be too small to optimally image the vessel 84. For this reason, a medical practitioner has the option of selecting a number of transmit focal positions, e.g., two focal positions as indicated by the cursors 86, 88 on the right hand side of the viewing screen 44, as shown in FIG. 5. The positions of the focal positions are adjusted by suitable means, such as by manipulating a control of the control panel 38.

The two transmit focal positions are used by first transmitting a beam of ultrasound focused at the first focal position. Ultrasound reflections are then obtained as explained above, and a first set of data corresponding thereto are stored by suitable means. A second beam of ultrasound focused at the second focal position is then transmitted, and ultrasound reflections are then also obtained and a second set of data corresponding thereto are stored. The image 80 is then formed using both sets of stored data, with the portion of the image in the first focal position predominantly derived from the first set of data and the portion of the image in the second focal position predominantly derived from the second set of data. A preferred way to employ multiple transmit focal regions is described in U.S. Pat. No. 6,315,723.

The operation of the system 10 has been explained with reference to the B-mode images shown in FIGS. 4 and 5. However, it will be understood that the same principles apply to other types of images, such as Doppler images.

Although the system 10 can be operated as explained with reference to FIGS. 4 and 5 to optimally position the transmit focal position(s), it nevertheless has its limitations and problems. For example, it can be fairly time consuming to place the transmit focal positions in the correct position. Additionally, it can require an extraordinary level of expertise to select the proper number of focal positions and correctly position each of the focal positions at the optimal location. For these and other reasons, the focal position(s) are often not positioned in the optimal location, and, in many instances, practitioners do not even attempt to optimally position focal positions. In fact, practitioners are sometimes not even aware that the position of the focal position can be adjusted or that multiple focal positions can be used. There is therefore a need for a system and method that can quickly and easily select the optimal number of focal positions and their optimum positions without the need for extraordinary operating expertise.

SUMMARY OF THE INVENTION

An ultrasound diagnostic imaging system and method uses an image processor that automatically sets the location of a focal position of the beam of ultrasound transmitted by an ultrasound scanhead based on an analysis of an ultrasound image displayed on an ultrasound display. The image processor may analyze the image to automatically identify an area of interest, or the area of interest may be selected manually by a user. The image processor may automatically identify the area of interest by analyzing a characteristic of the image, such as the quality of the image. The image processor may set the location of the focal position to correspond to the position of an area of interest, to maximize the quality of the ultrasound image in the area of interest, or by some other means. The image processor may also select the number of ultrasound transmissions and the locations of respective focal positions based on an analysis of the ultrasound image. The image processor may also dynamically vary the position of a focal position by varying the location of the focal position along a depth axis as a function of the locations of areas of interest along an azimuth axis of the ultrasound display.

DETAILED DESCRIPTION OF THE INVENTION

Figure 6:
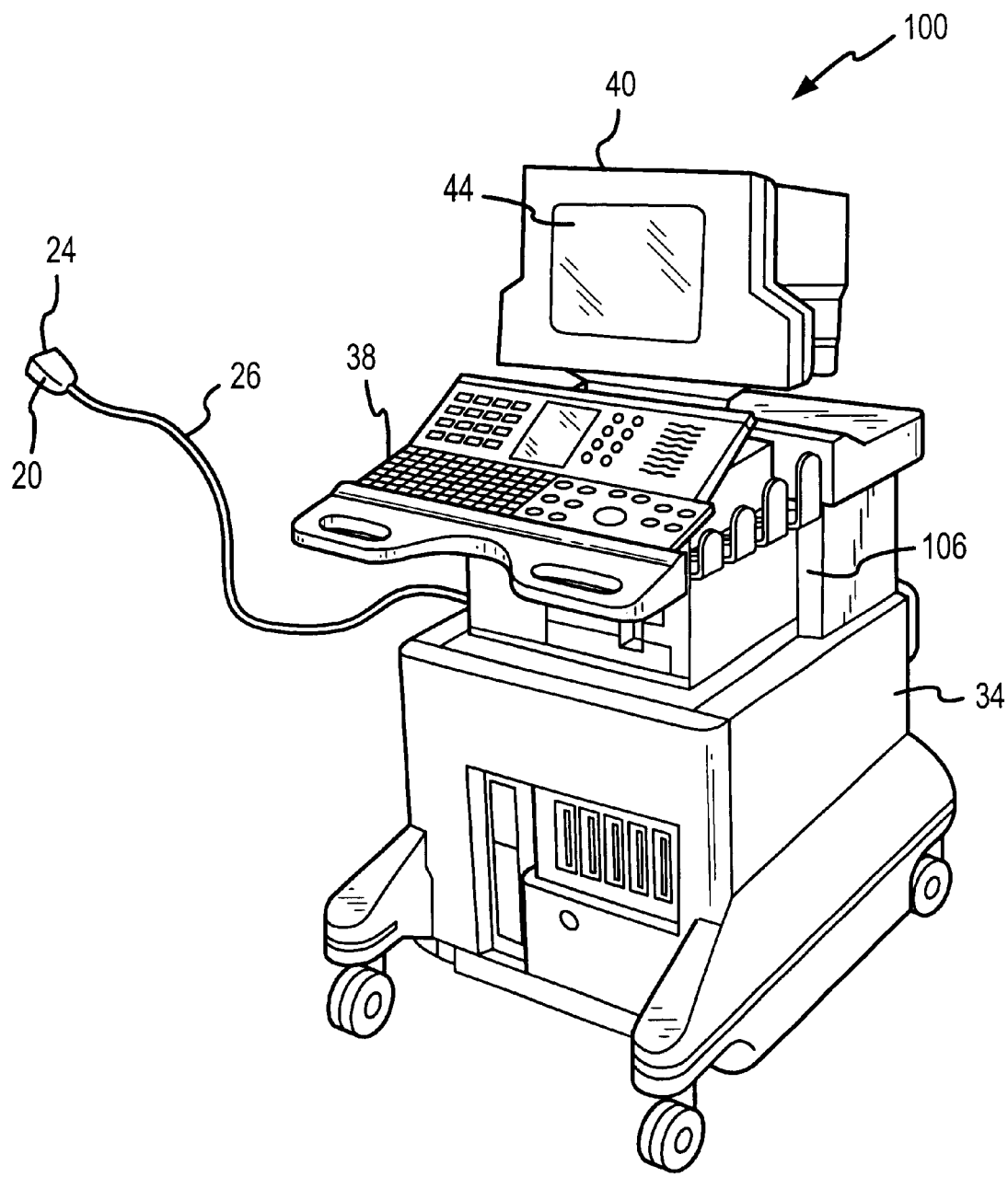
FIG. 6 is an isometric view of one embodiment of a diagnostic ultrasound imaging system according to the present invention.

One embodiment of an ultrasound imaging system 100 according to the present invention is shown in FIG. 6. The system 100 uses many of same components used in the imaging system 10 of FIG. 1. Therefore, in the interests of brevity, these components have been provided with the same reference numerals, and an explanation of their function and operation will not be repeated. The system 100 differs from the system 10 shown in FIG. 1 primarily by using an imaging unit 106 that is different from the imaging unit 30 used in the system 10. The components used in the imaging unit 106 will be explained below with reference to FIG. 11.

Figure 7:
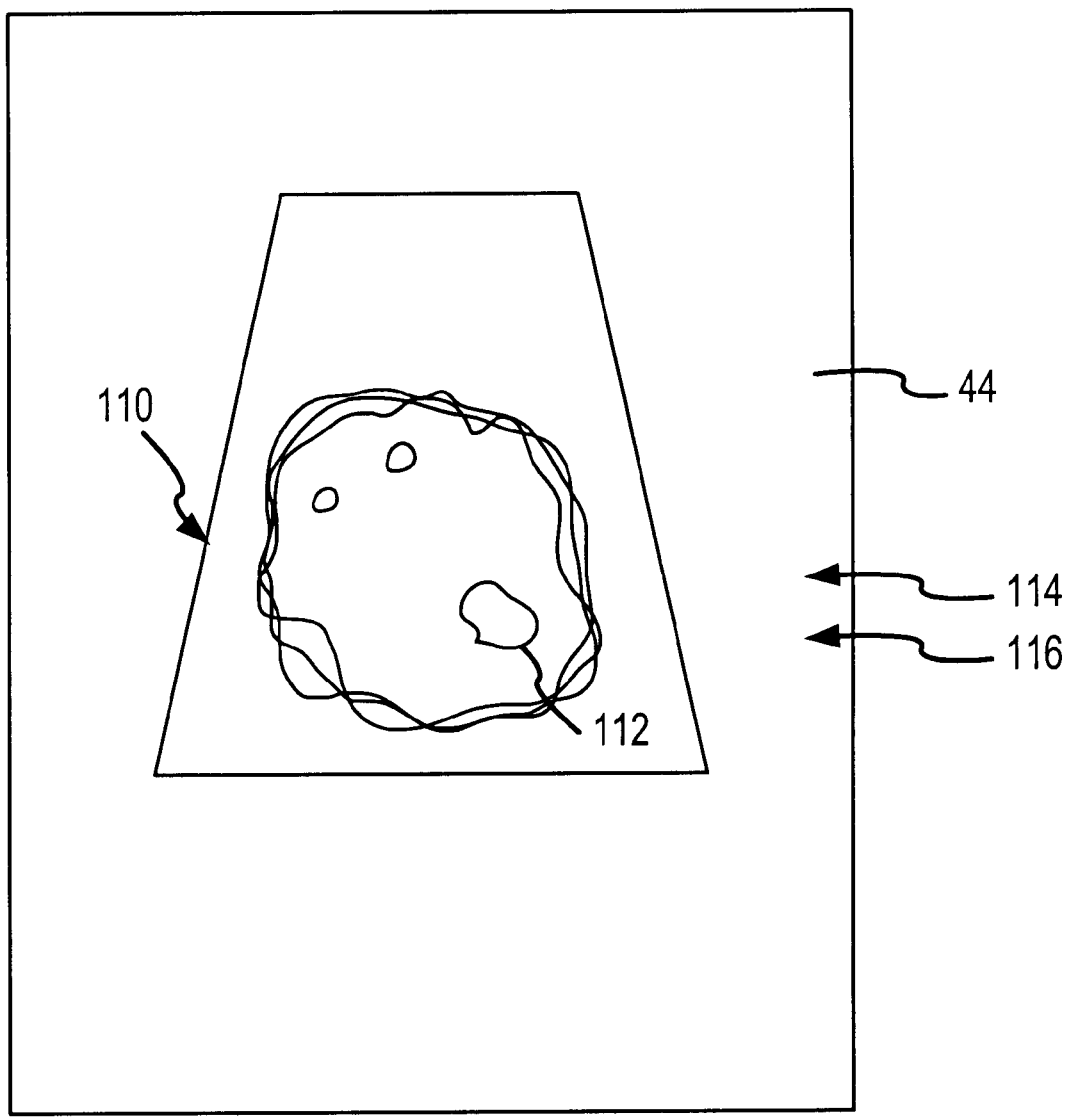
FIG. 7 is a schematic illustration of an ultrasound image shown on the viewing screen of the ultrasound imaging system of FIG. 6 in accordance with one embodiment of the invention.

The system 100 can generate an ultrasound image 110 in accordance with one embodiment of the invention, as shown in FIG. 7. The system 100 generates the image 110 by automatically analyzing the image 110 to locate an area of interest 112 by suitable means. The system 100 may perform this analysis using presently existing algorithms for analyzing ultrasound images, although subsequently developed algorithms for analyzing ultrasound images may also be used. In one embodiment, the algorithm analyzes the image 110 to locate the brightest area, and this area is selected as the area of interest. In another embodiment, "tissue specific imaging" is used in which the characteristics of expected areas of interest are defined by the type of image being obtained. With "tissue specific imaging," available on the Philips HDI 5000 ultrasound system, the user selects the anatomy to be imaged and the ultrasound system automatically initializes itself with preferred parameters for scanning the anatomy. For example, the user may select "obstetric imaging" or "cardiac imaging." In obstetric scanning, the expected areas of interest will be in relatively bright areas of the image. For cardiac imaging, the area of interest can be defined by image characteristics of specific areas of the heart, such as the left ventricle or a mitral valve.

Based on factors such as the size of the area of interest, the location of bright objects in the image, the identity of the anatomy of interest such as a fetus in obstetric imaging or the heart in cardiac imaging, statistical analysis (homogeneity, distinctiveness of features, etc.) or other factors such as the current depth of focus of the transmit beam, the system 100 determines the number of focal positions that should optimally be used to generate the image 110. The system 100 then places cursors 114, 116 on the right hand side of the viewing screen 44 to indicate the position of each transmit focal position. In one embodiment of the invention, the user may manually adjust these automatically determined positions by suitable means, such as by manipulating a control on the control panel 38.

Figure 8:
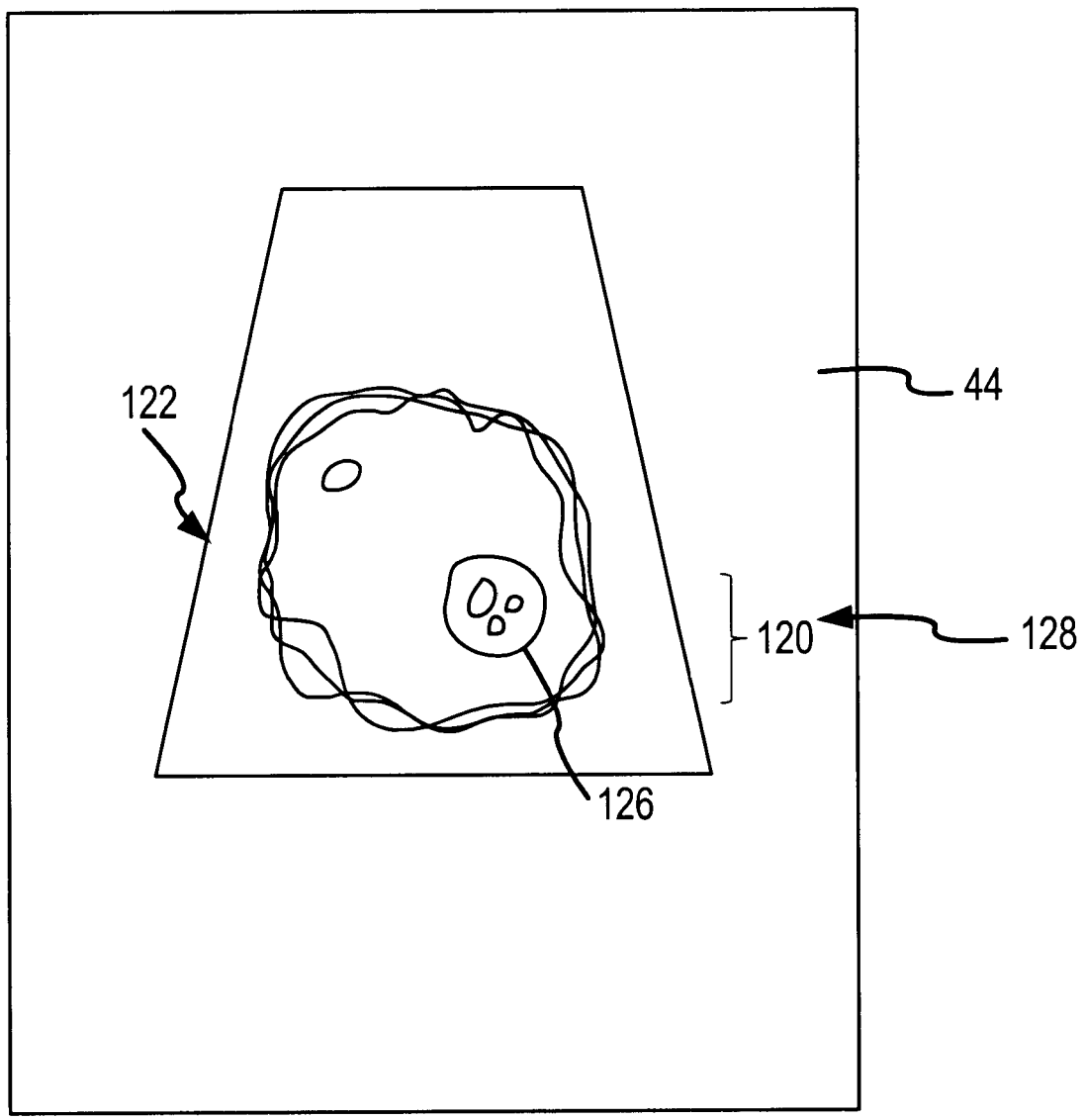
FIG. 8 is a schematic illustration of an ultrasound image shown on the viewing screen of the ultrasound imaging system of FIG. 6 in accordance with another embodiment of the invention.

In another embodiment of the invention shown in FIG. 8, the system 100 allows a user to designate an area of interest 120 in an image 122 by suitable means, such as by using a pointing device like a mouse, trackball, or light pen, or by touching the displayed area of interest on a touch-panel display. The system 100 then determines from this user input the location of the transmit focal position or number and locations of multiple transmit focal positions that will be used to be used to generate a subsequent version of the image 122. The system also preferably delineates the area of interest 120 selected by the user with a segmenting border 126 or other indicia, and places a cursor 128 on the right hand side of the viewing screen 44 to show the position of the focal position along the depth axis.

A preferred technique for automated border segmentation is described in U.S. patent [application Ser. No. 09/732,613], entitled "Automated Border Detection in Ultrasonic Diagnostic Images. As described therein, the image data of a structure such as the heart is analyzed to identify specific anatomical features, such as the location of the mitral valve plane and the boundaries of the myocardium. If diagnosis of the mitral valve performance is of interest to the clinician, for instance, the identification of the mitral valve plane will identify the depth of the mitral valve in the ultrasound image. Automated border detection may be used to identify other structures in the body, such as anatomy of the fetus in an obstetrical patient. An embodiment of the present invention using automated border detection identifies the anatomy of interest, then the depth of the identified anatomy is used to set the number and/or location of the focal position(s) in an ultrasound image.

Since automated border detection can operate on time sequential images, the technique can be employed to analyze image data periodically or continuously, and therefore can track anatomical features over time. This information can be used to update the focal position periodically or continuously, thus constantly optimizing the focus even in the presence of scanhead or anatomical motion. Preferably some form of hysteresis or integration is used so that the focal position is not changed and does not appear to jitter for small motional changes.

As previously mentioned, the frame rate of the system 100 decreases with an increase in the number of focal positions used. In one embodiment, the user may limit the number of multiple focal position which the system may use, the minimum acceptable frame rate, or select the degree to which the automatic selection of multiple transmit focal positions is discouraged. In this embodiment, the system 100 may select the use of multiple focal positions, but it will do so only where the use of multiple transmit focal positions is very important to the quality of the image 110. In other embodiments where frame rate performance limitations do not exist, the system 100 may automatically select the use of multiple focal positions whenever multiple focal positions would noticeably improve the quality of the image.

Figure 9:
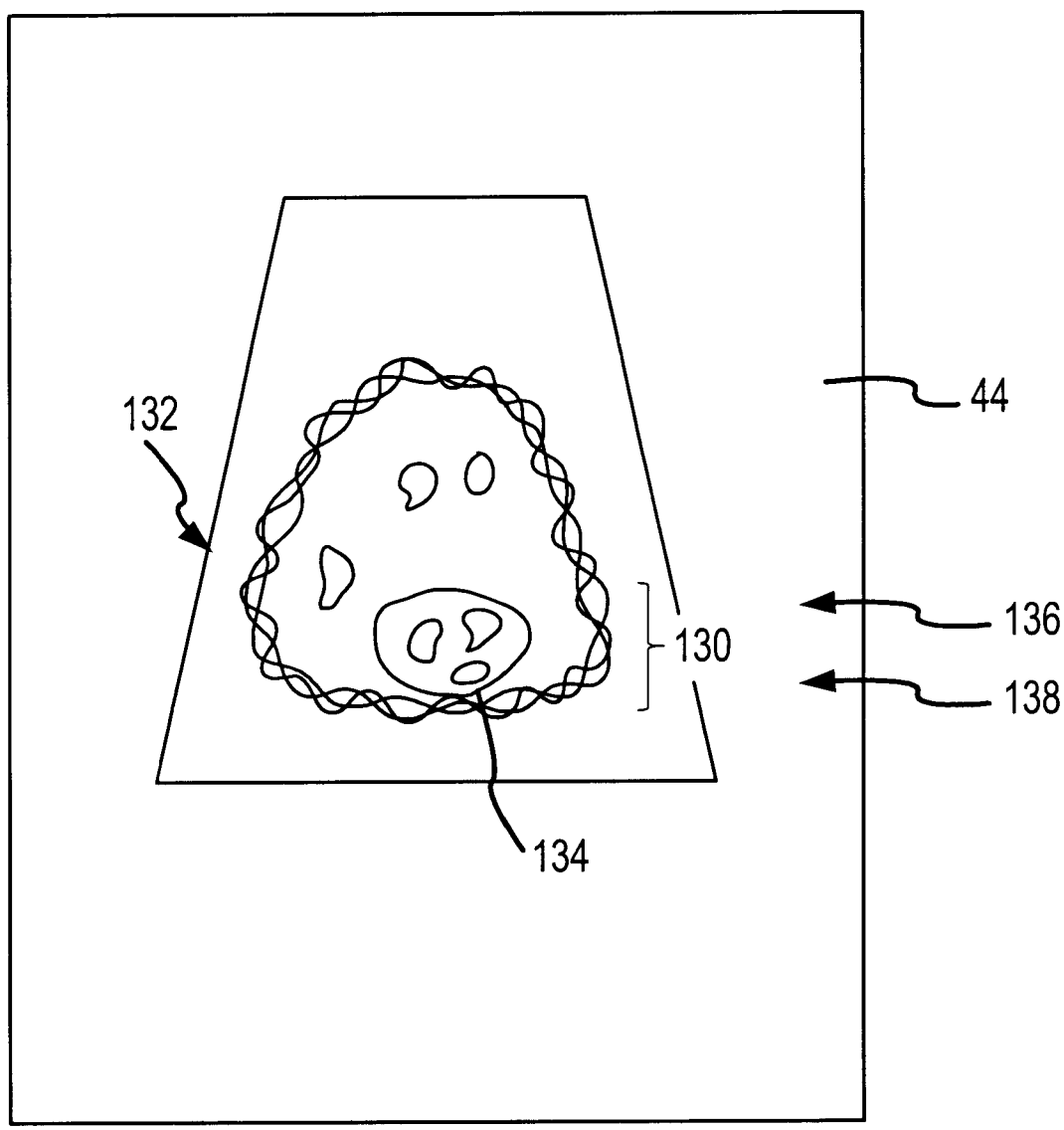
FIG. 9 is a schematic illustration of an ultrasound image shown on the viewing screen of the ultrasound imaging system of FIG. 6 in accordance with a further embodiment of the invention.

In another embodiment of the invention shown in FIG. 9, the system 100 either automatically selects an area of interest 130 in an image 132 or allows a user to designate the area of interest 130 by suitable means, such as by using a pointing device or by delineating the area with a segmenting border 134. The system 100 then automatically analyzes the quality of the image 132 in the area of interest 130 by a conventional or hereinafter developed algorithm, such as by analyzing the sharpness of image detail. After each analysis of the area of interest 130, the system 100 alters the position of the focal position and/or the number of focal positions used until the optimum position of the focal position is determined. The system 100 also preferably places cursors 136, 138 at the right hand edge of the viewing screen to indicate the number of focal positions used to create the image 132 and their respective positions. Also, techniques can be used to limit the amount of processing needed to determine the location of focal position(s) by, for example, limiting the frequency at which the focal position(s) are calculated or using hysteresis or thresholding so that a new focal position is calculated only for relatively large changes in factors used to determine the position of the focal position (s).

Figure 10:
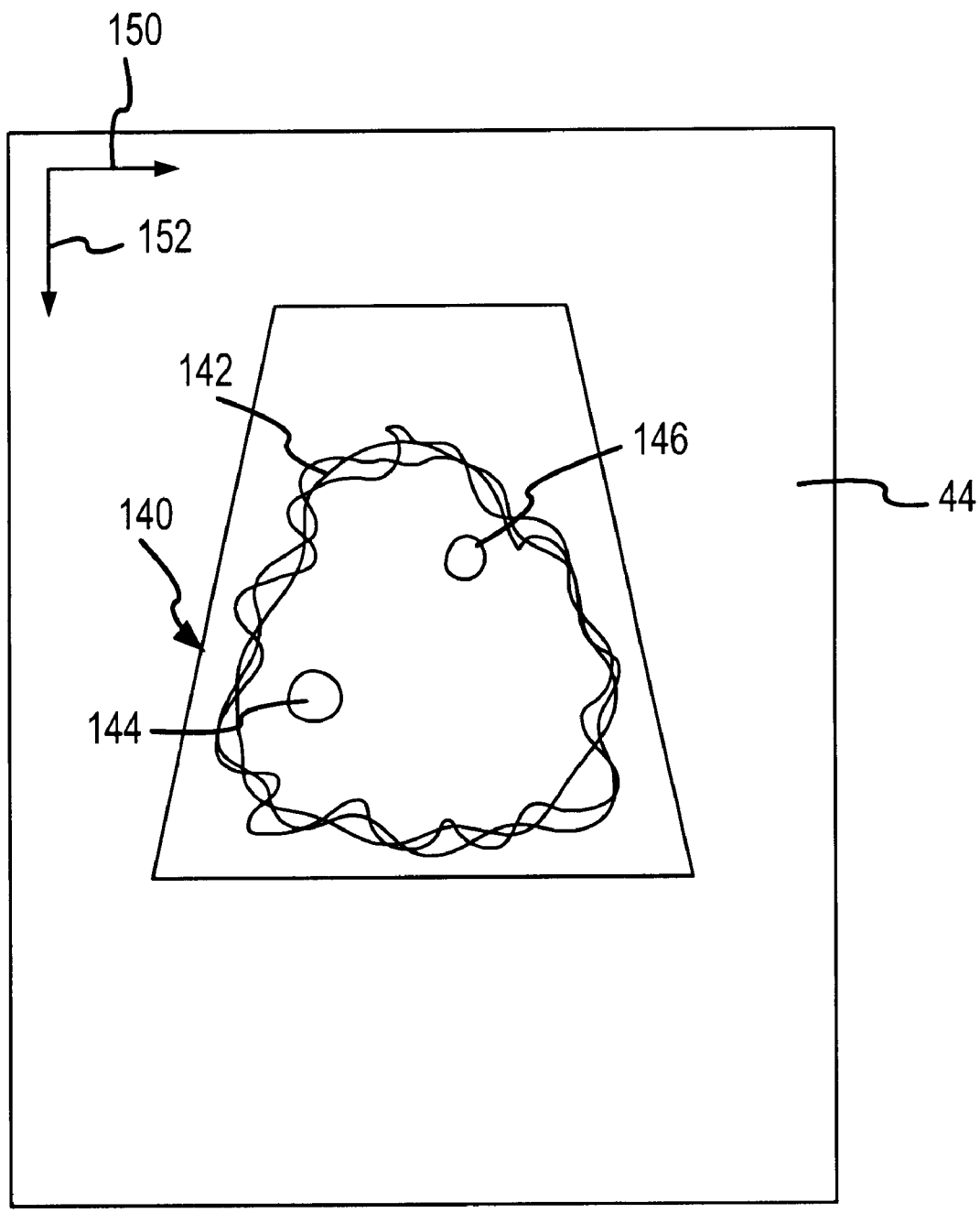
FIG. 10 is a schematic illustration of an ultrasound image shown on the viewing screen of the ultrasound imaging system of FIG. 6 in accordance with still another embodiment of the invention.

In still another embodiment of the invention shown in FIG. 10, the system 100 solves the aforementioned problem of selecting the location of a transmit focal position where two areas of interest are located at different depths. The areas of interest may be located either automatically or through user input, as explained above. As shown in FIG. 10, an image 140 on the viewing screen 44 includes tissues 142 containing a first blood vessel 144 and a second blood vessel 146. The first blood vessel 144 is positioned at a first location along an azimuth axis 150, i.e., at the left hand side of the viewing screen 44, and at a first location along a depth axis 152, i.e., near the bottom of the viewing screen 44. The second blood vessel 146 is positioned at a second location along the azimuth axis 150, i.e., at the right hand side of the viewing screen 44, and at a second location along a depth axis 152, i.e., toward the top of the viewing screen 44. The different locations of the vessels 144, 146 along the depth axis 152 precludes any single location of a focal position from being optimum to image both vessels 144, 146. Two different focal positions may be used, one located at the depth of the first blood vessel 144 and the other located at the depth of the second blood vessel 146. However, this approach would reduce the frame rate of the imaging system 100.

According to one embodiment of the invention, after the areas of interest, e.g., the blood vessels 144, 146, are selected either automatically or manually, as previously described, the system 100 automatically alters the position of one or more focal positions along the depth axis 152 as a function of the position of each area of interest along the azimuth axis 150. When the system 100 is imaging the blood vessel 144 on the left hand side of the image 140, the system 100 selects a location for the focal position that corresponds to the position of the blood vessel 144 along the depth axis of the image 140. When the system 100 is imaging the blood vessel 146 on the right hand side of the image 140, the system 100 selects a location for the focal position that corresponds to the position of the blood vessel 146 along the depth axis of the image 140. As a result, the position of the focal position is dynamically variable along the depth axis 152, which can even be accomplished within a common image frame, a benefit made possible when the areas of interest occupy different lateral areas of the image.

The embodiment of the invention explained with reference to FIG. 10 may also be combined with other embodiments. For example, each of the areas of interest in the image 140 may be selected by automatically analyzing the image 140 as explained above with reference to FIG. 7 or by allowing a user to designate the areas of interest as explained above with reference to FIG. 8. The dynamically varying locations of the focal position may also be set using the techniques explained above, such as by optimizing the quality of the image 140 in predetermined areas as explained above with reference to FIG. 9. Other combinations and alternatives will be apparent to one skilled in the art.

Figure 1:
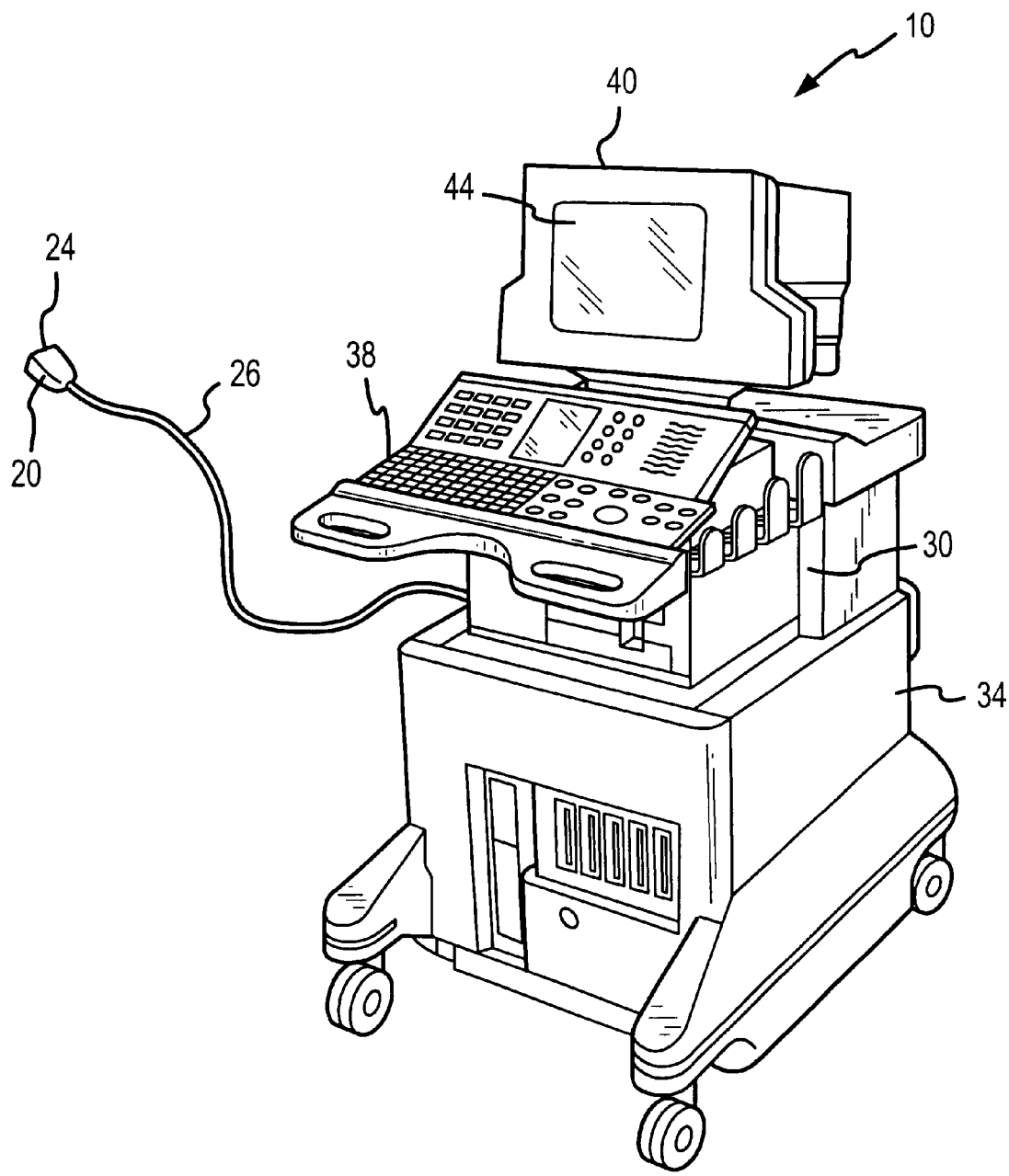
FIG. 1 is an isometric view of a conventional diagnostic ultrasound imaging system.
Figure 2:
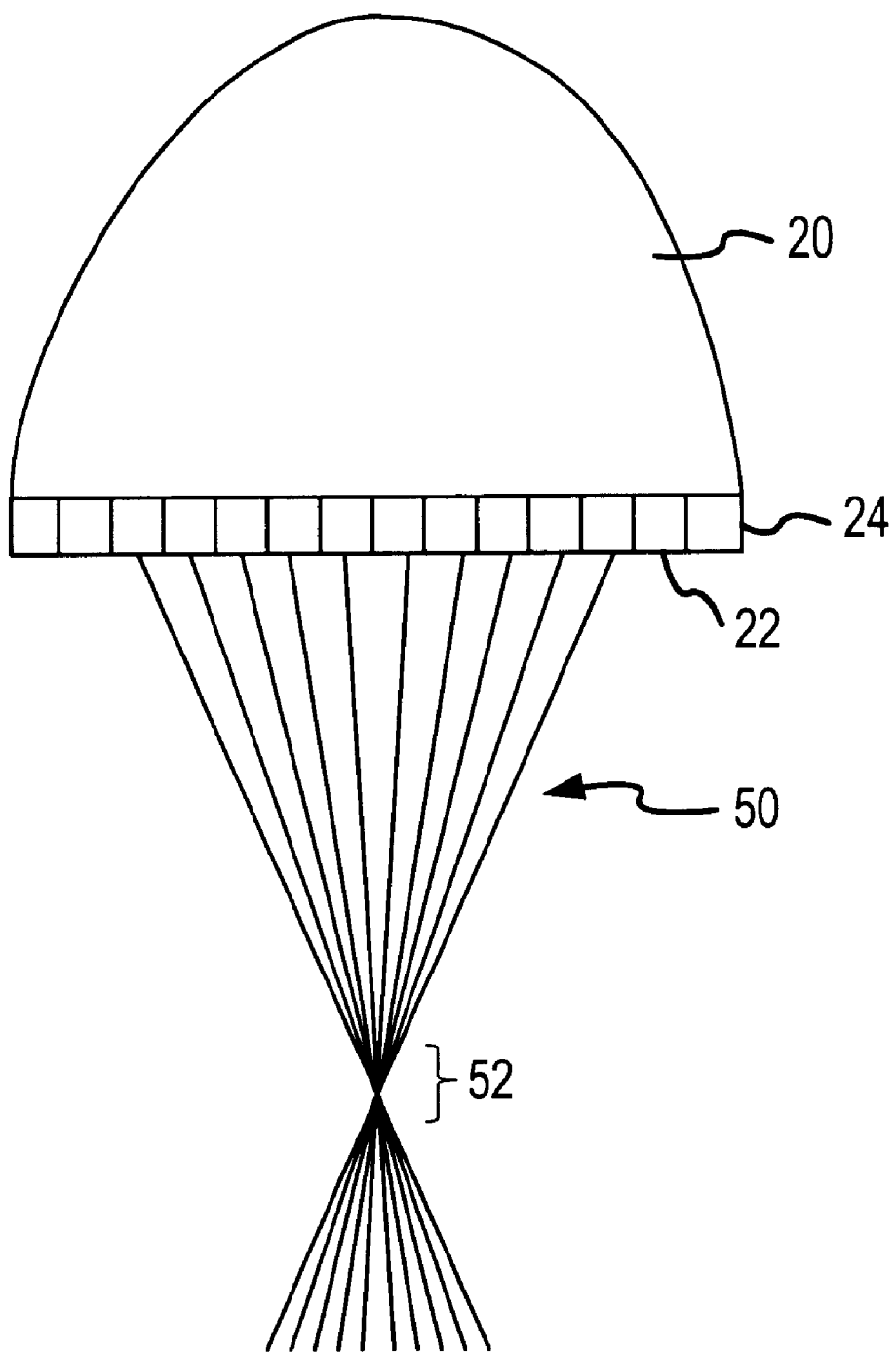
FIG. 2 is a schematic diagram illustrating the manner in which an ultrasound scanhead used in the system of FIG. 1 transmits a beam of ultrasound energy responsive to electrical signals.
Figure 3:
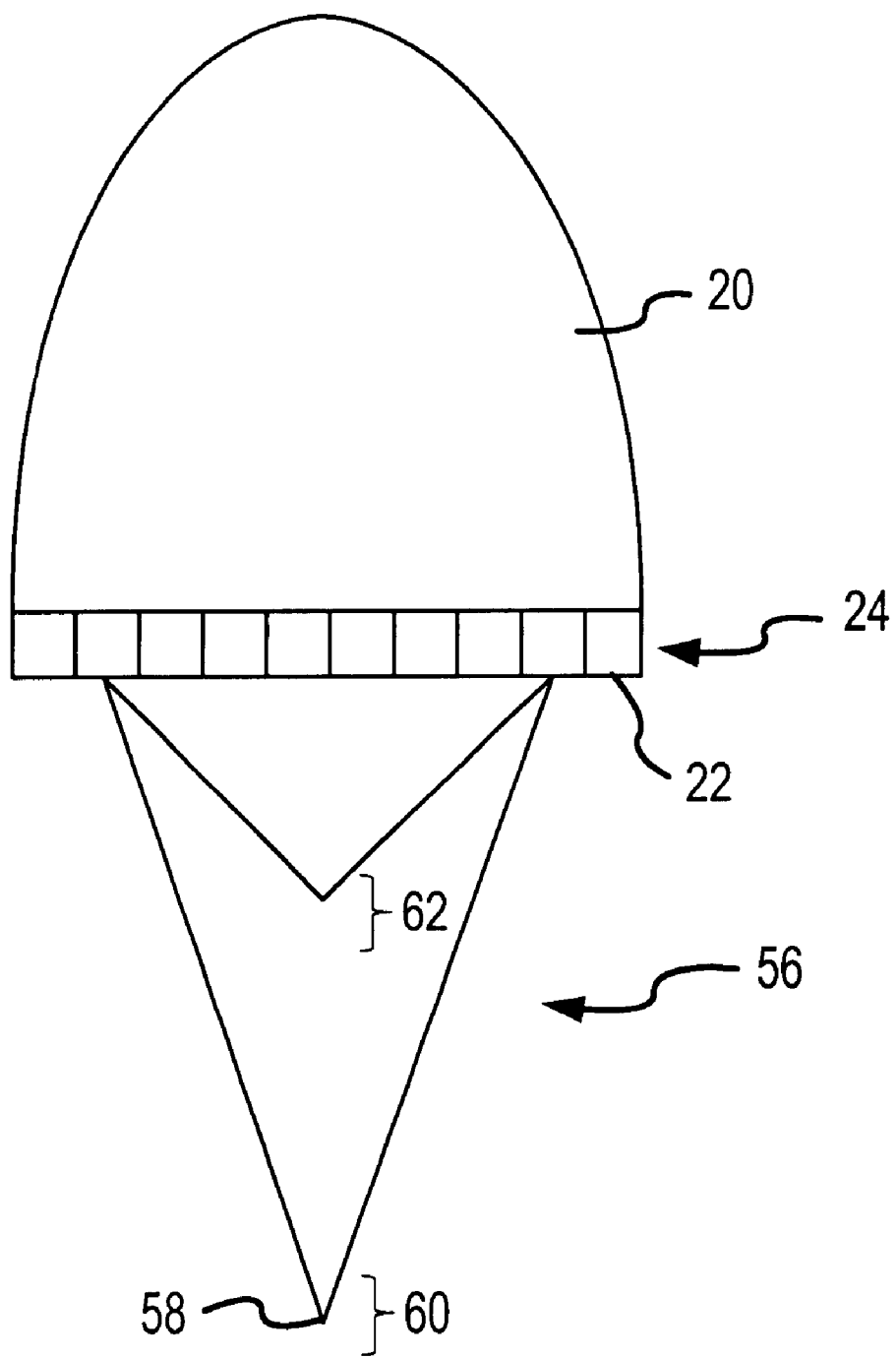
FIG. 3 is a schematic diagram illustrating the manner in which an ultrasound scanhead used in the system of FIG. 1 receives a beam of ultrasound energy and generates corresponding electrical signals.
Figure 4:
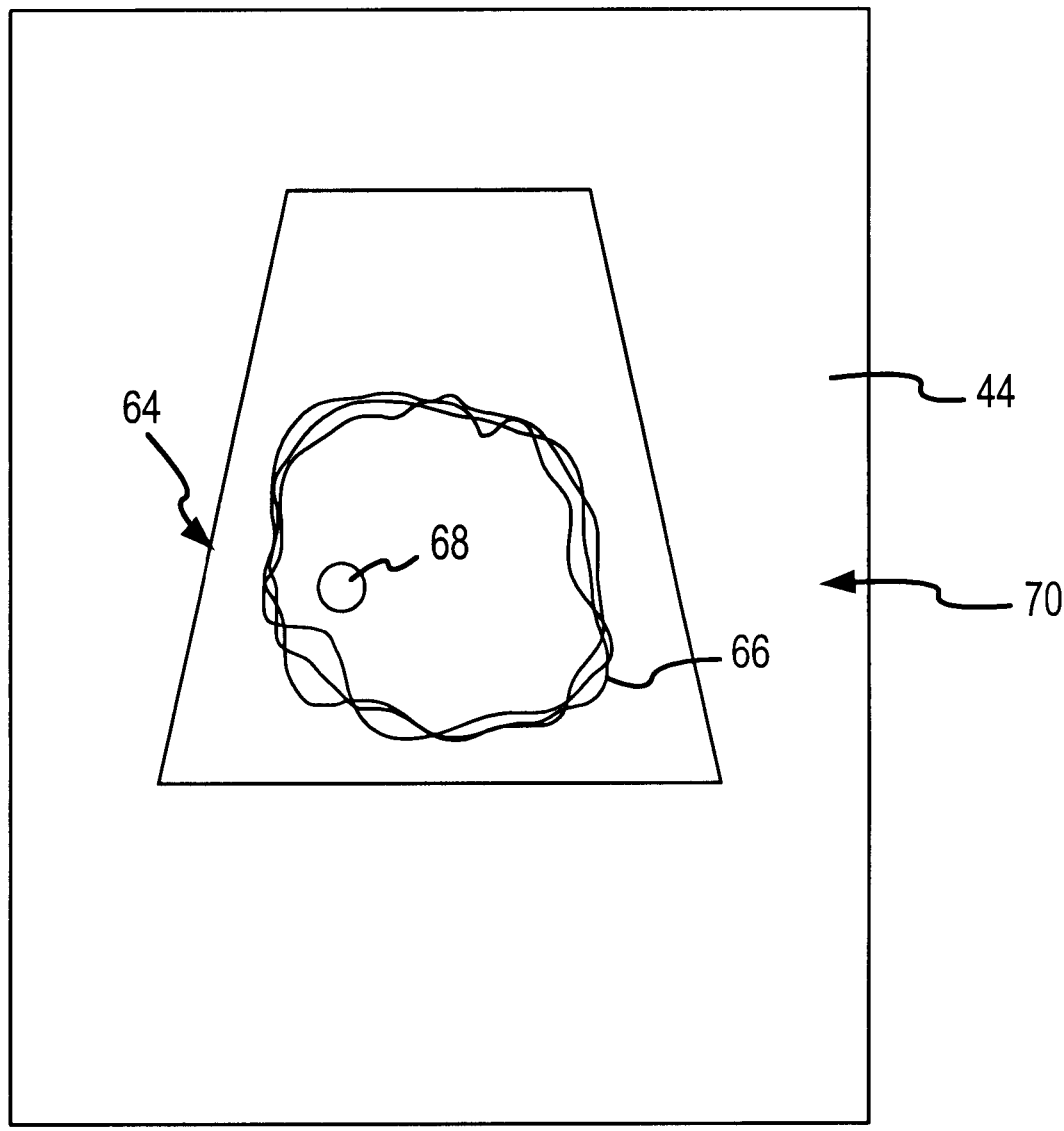
FIG. 4 is a schematic illustration of an ultrasound image shown on the viewing screen of a display in a conventional ultrasound imaging system.
Figure 5:
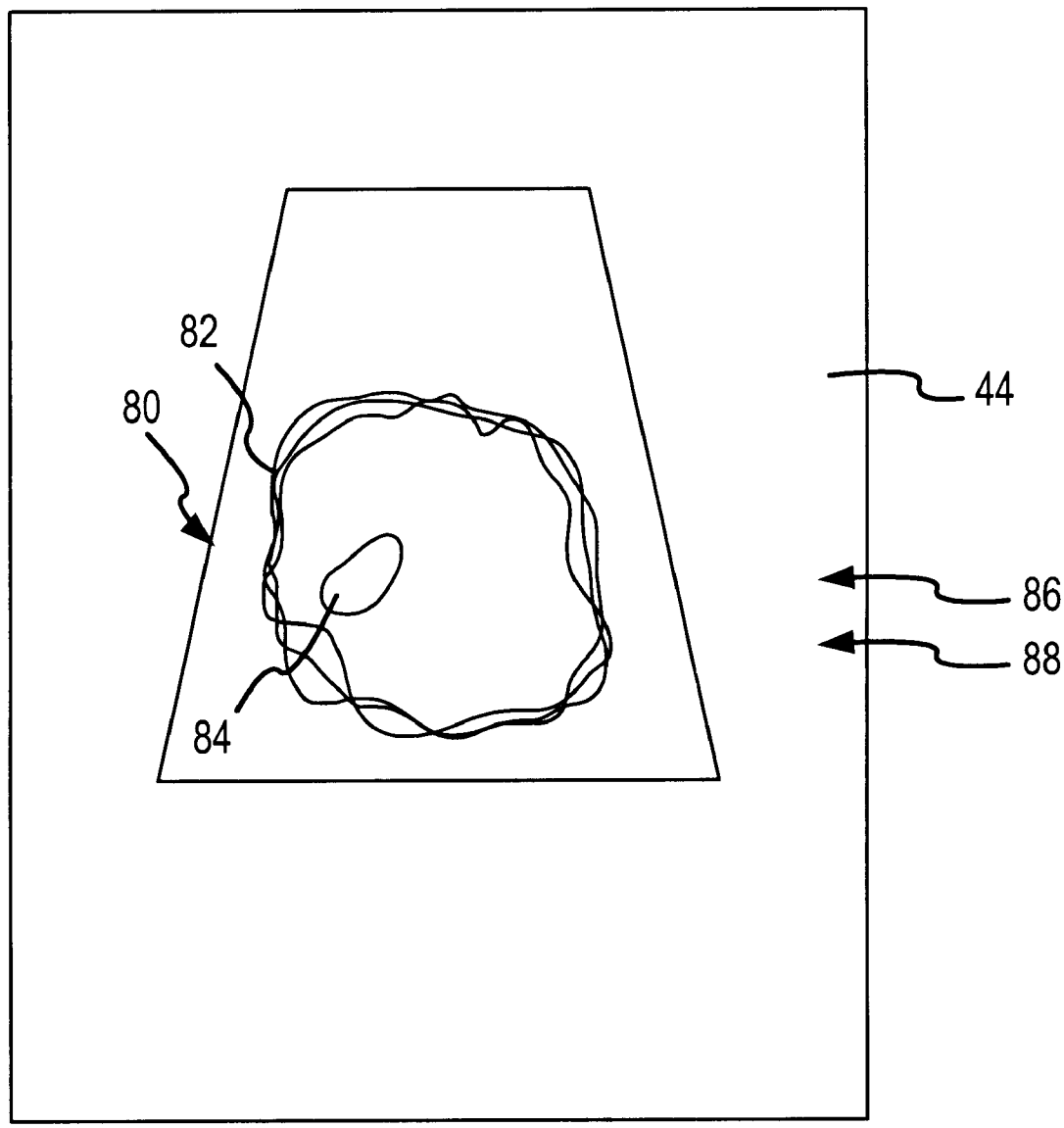
FIG. 5 is a schematic illustration of an ultrasound image shown on the viewing screen of a display in a conventional ultrasound imaging system in which the ultrasound image is generated using two separate focal positions.

In operation, the user may manually initiate setting the location of the one or more focal positions by suitable means, such as by pressing a key on the control panel 38 (FIG. 1). Alternatively, the system 100 may operate in the background to periodically set the location of the one or more focal positions. Other means of initiating the setting of the focal positions can also be used.

Figure 11:
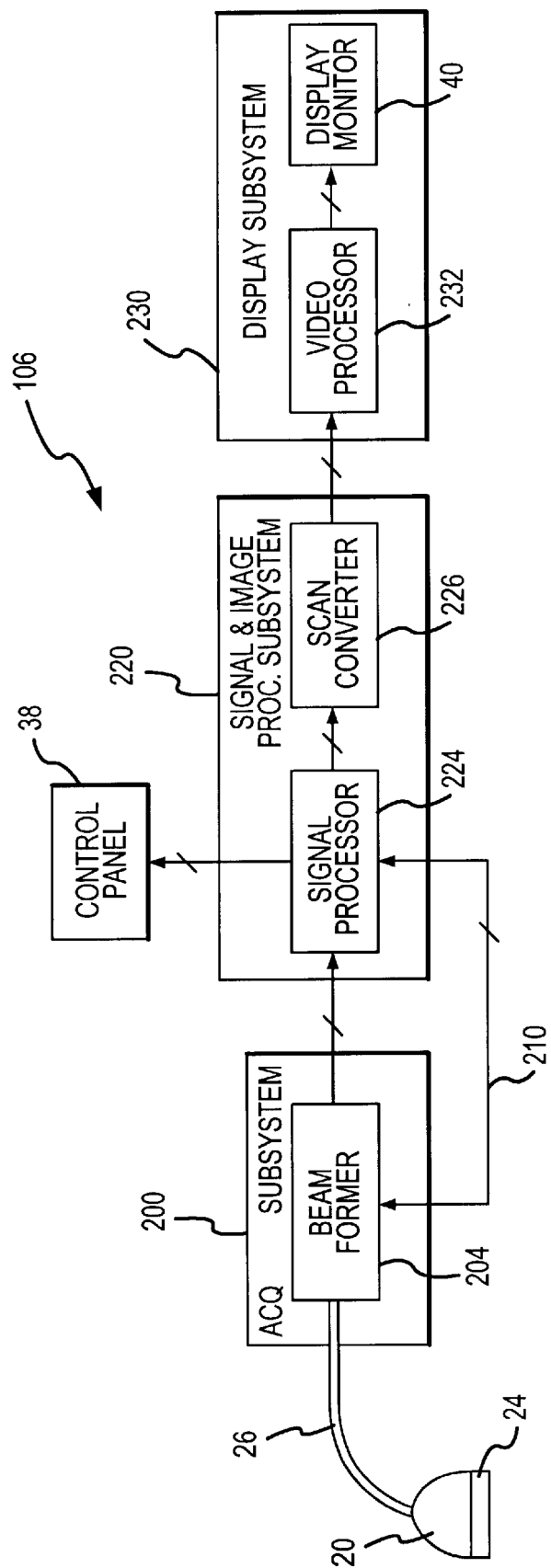
FIG. 11 is a block diagram of one embodiment of an imaging unit according to the present invention that may be used in the ultrasound imaging system of FIG. 6.

One embodiment of the imaging unit 106 used in the system of FIG. 6 is shown in FIG. 11. The imaging unit 106 includes an acquisition subsystem 200 that includes a beamformer 204 coupled to the scanhead 20 through the cable 26. Electric signals from the transducer elements of scanhead 20 are applied to the beamformer 204, which processes signals corresponding to echoes of each acquired scanline into a beam. As explained above, the beamformer 204 applies electrical signals to the transducer elements 26 in the scanhead 20 to cause the scanhead to transmit a beam of ultrasound energy. The beamformer 204 controls the respective delays of the signals applied to the transducer elements of scanhead 20 to focus the transmit beam to a specific depth. The location of the focal position is controlled by control data applied through a control line 210.

The received signals from the beamformer 204 are applied to a Signal & Image Processing subsystem 220, which includes a conventional signal processor 224 and a conventional scan converter 226. The signal processor 224 receives the signals from the beamformer 204 to generate image data corresponding to an image, such as the images shown in FIGS. 7–10. The signal processor 224 may also analyze the image data corresponding to a predetermined portion of the image to determine the optimum location of the focal position or the optimum number of focal positions and their optimum locations, as explained above with reference to FIGS. 7–10. The signal processor 224 also interfaces with the control panel 38 (not shown) to receive user input, such as a command to initiate the focal position adjustment process or information designating an image area that should be analyzed for quality, as explained above. After the signal processor 224 determines the optimum location of the focal position or the optimum number of focal positions and their optimum locations, it applies appropriate control data to the beamformer over control line 210 to control the location of the focal position(s). The signal processor 224 can also couple other data to the beamformer 204, such as data controlling the sizes of the transmit and receive apertures. The image data from the signal processor are then applied to the scan converter 226, which arranges the image data into respective ultrasonic image frame data of the desired image format.

The image frame data from the Signal & Image Processing subsystem 220 are then transferred to a display subsystem 230, which includes a video processor 232 and the display monitor 40. The video processor 232 converts the image frame data from the scan converter 226 into appropriate video signals, such as NTSC or SVGA video signals, for use by the display monitor 40.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of automatically setting focal positions of a set of beam of transmitted ultrasound in an ultrasound imaging system having a display on which an ultrasound image is generated, the ultrasound display having a depth axis and an azimuth axis, the method comprising:
   automatically analyzing the ultrasound image to identify an area of interest in the ultrasound image; and
   automatically setting the location of the focal positions of the beams of transmitted ultrasound to correspond to the location of the area of interest of the ultrasound image.

2. The method of claim 1 wherein the act of automatically setting the location of the focal positions of the beams of transmitted ultrasound comprises automatically setting respective locations of at least two focal positions along the depth axis of the ultrasound display.

3. The method of claim 2 wherein the act of setting respective locations of at least two focal positions along the depth axis of the ultrasound display comprises setting the respective locations of the focal positions along the depth axis of the ultrasound display for respective locations along the azimuth axis of the ultrasound display.

4. The method of claim 1 wherein the act of automatically setting the location of the focal positions of the beams of transmitted ultrasound to correspond to the location of the area of interest of the ultrasound image comprises automatically setting the number of focal positions and the location of each focal position.

5. The method of claim 1 wherein the act of automatically analyzing the ultrasound image to identify an area of interest in the ultrasound image comprises automatically analyzing the ultrasound image to identify a predetermined image characteristic.

6. The method of claim 5, wherein the act of automatically analyzing the ultrasound image to identify a predetermined image characteristic comprises analyzing image data by automated border detection.

7. The method of claim 5, wherein the act of analyzing image data by automated border detection comprises analyzing the image data of temporally different images, and wherein the act of automatically setting the location of the focal positions of the beams comprises updating the location of the focal positions of the beams at least periodically.

8. The method of claim 1 wherein the act of automatically analyzing the ultrasound image to identify an area of interest in the ultrasound image comprises analyzing the quality of the image in a predetermined area of the image.

9. The method of claim 8 wherein the act of automatically setting the locations of the focal positions of the beams of transmitted ultrasound comprises setting the locations of the focal positions to optimize the quality of the image in the predetermined area.

10. A method of setting focal positions of beams of transmitted ultrasound in an ultrasound imaging system having a display on which an ultrasound image is generated, the ultrasound display having a depth axis and an azimuth axis, the method comprising:
   viewing the ultrasound image;
   selecting an area of interest in the ultrasound image; and
   automatically setting the location of the focal positions of beams of transmitted ultrasound based on a characteristic of the selected area of interest of the ultrasound image.

11. The method of claim 10 wherein the act of selecting an area of interest comprises selecting a plurality of areas of interest in the ultrasound image along both the depth axis and the azimuth axis, and wherein the act of automatically setting the location of the focal positions of the beams of transmitted ultrasound comprises automatically setting the location of a respective focal position of the beams of transmitted ultrasound based on a characteristic of each of the selected areas of interest of the ultrasound image.

12. The method of claim 11 wherein the act of automatically setting the location of the focal positions of the beams of transmitted ultrasound based on the location of the selected area of interest comprises automatically setting the focal positions to a plurality of locations along the depth axis of the ultrasound display for respective locations along the azimuth axis of the ultrasound display.

13. The method of claim 10 wherein the act of automatically setting the location of the focal positions of the beams of transmitted ultrasound based on the location of the selected area of interest comprises setting respective locations of at least two focal positions along the depth axis of the ultrasound display.

14. The method of claim 10 wherein the act of automatically setting the location of the focal positions of the beams of transmitted ultrasound based on a characteristic of the selected area of interest comprises automatically setting the locations of the focal positions to maximize the quality of the image in the selected area.

15. The method of claim 10 wherein the act of selecting an area of interest in the ultrasound image comprises placing an identifying marking on the ultrasound display at a location corresponding to the location of the selected area of interest which segments the selected area of interest.

16. The method of claim 10 wherein the act of automatically setting the location of the focal positions of the beams of transmitted ultrasound based on a characteristic of the selected area of interest comprises automatically setting the number of focal positions and the location of each focal position based on a characteristic of the selected area of interest.

17. An ultrasound imaging system comprising:
a scanhead having an array of ultrasound transducers;
a beamformer coupled to the scanhead, the beamformer applying electrical signals to the scanhead to cause the scanhead to transmit beams of ultrasound and receiving electrical signals from the scanhead responsive to ultrasound echoes received by the scanhead, the beams of ultrasound transmitted by the scanhead being focused in a focal position determined by a control signal applied to the beamformer;
an image processor coupled to receive signals from the beamformer, the image processor converting the signals to image data corresponding to an ultrasound image, the image processor being operable to analyze the image data to identify an area of interest in an ultrasound image corresponding to the image data, the image processor further being operable to generate the control signal to set the location of the focal position of the beams of transmitted ultrasound to correspond to the location of the area of interest of the ultrasound image; and
a display coupled to the image processor, the display generating an ultrasound image corresponding to the image data.

18. The ultrasound imaging system of claim 17 wherein the image processor is further operable to apply signals to the beamformer to cause the beamformer to transmit at least two beams of ultrasound having respective focal positions, the positions of the focal positions being controlled by signals applied to the beamformer by the image processor.

19. The ultrasound imaging system of claim 17 wherein the image processor is further operable to apply signals to the beamformer to set the respective locations of the focal positions along a depth axis of the ultrasound display.

20. The ultrasound imaging system of claim 17 wherein the image processor is operable to analyze the ultrasound image to identify a predetermined image characteristic.

21. The ultrasound imaging system of claim 20, wherein the image processor comprises an automated border detection processor which is operable to automatically identify a predetermined image feature.

22. The ultrasound imaging system of claim 17 wherein the ultrasound transducers in the scanhead are arranged in a linear array.

23. An ultrasound imaging system comprising:
a scanhead having an array of ultrasound transducers;
a beamformer coupled to the scanhead, the beamformer applying electrical signals to the scanhead to cause the scanhead to transmit a beam of ultrasound and receiving electrical signals from the scanhead responsive to ultrasound echoes received by the scanhead, the beam of ultrasound transmitted by the scanhead being focused in a focal position determined by a control signal applied to the beamformer;
a user interface device structured to allow a user to enter information, including information identifying an area of interest in an ultrasound image along both a depth axis and an azimuth axis;
an image processor coupled to receive signals from the beamformer and from the user interface, the image processor converting the signals to image data corresponding to an ultrasound image;
a control line, responsive to the user interface device, the control line further being operable to couple the control signal to set the location of the focal position of the beam of transmitted ultrasound based on the entered information; and
a display coupled to the image processor, the display generating an ultrasound image corresponding to the image data.

24. The ultrasound imaging system of claim 23 wherein the ultrasound transducers in the scanhead are arranged in a linear array.

25. The ultrasound imaging system of claim 23 wherein user interface device is structured to allow a user to enter information identifying a plurality of areas of interest in an ultrasound image, and wherein the control line is operable to apply signals to the beamformer to cause the beamformer to set the locations of respective focal positions of beams of transmitted ultrasound.

26. The ultrasound imaging system of claim 23 wherein the control line is operable to apply signals to the beamformer to cause the beamformer to transmit at least two beams of ultrasound having respective focal positions, the positions of the focal positions being controlled by signals applied to the beamformer by the control line.

27. An ultrasound imaging system comprising:
a scanhead having an array of ultrasound transducers;
a beamformer coupled to the scanhead, the beamformer applying electrical signals to the scanhead to cause the scanhead to transmit a beam of ultrasound and receiving electrical signals from the scanhead responsive to ultrasound echoes received by the scanhead, the beam of ultrasound transmitted by the scanhead being focused in a focal position determined by a control signal applied to the beamformer;

an image processor coupled to receive signals from the beamformer and from the user interface, the image processor converting the signals to image data corresponding to an ultrasound image, the image processor further being operable to generate the control signal to set the location of the focal position of the beam of transmitted ultrasound to correspond to the locations of a plurality of areas of interest along the depth axis as a function of the locations of the areas of interest along the azimuth axis; and a display coupled to the image processor, the display generating an ultrasound image corresponding to the image data.

28. The ultrasound imaging system of claim 27 wherein the image processor is operable to analyze the ultrasound image and to identify the plurality of areas of interest based on the analysis.

29. The ultrasound imaging system of claim 27, further comprising a user interface device structured to allow a user to enter information identifying the plurality of areas of interest.

30. The ultrasound imaging system of claim 27 wherein the image processor is operable to apply signals to the beamformer to cause the beamformer to set respective locations of at least two focal positions along the depth axis of the ultrasound display.

* * * * *